United States Patent [19]

Cannon

[11] Patent Number: 4,474,206
[45] Date of Patent: Oct. 2, 1984

[54] APPARATUS FOR, AND METHOD OF, CONTROLLING THE FLOW OF FLUID

[75] Inventor: Raymond E. Cannon, San Diego, Calif.

[73] Assignee: Imed Corporation, San Diego, Calif.

[21] Appl. No.: 365,774

[22] Filed: Apr. 5, 1982

[51] Int. Cl.³ .......................................... A61M 23/00
[52] U.S. Cl. ................................ 137/486; 137/487.5; 604/253
[58] Field of Search ..................... 137/486, 487.5, 460; 604/253, 251

[56] References Cited

U.S. PATENT DOCUMENTS 4,105,028  8/1978  Sadlier ......................... 137/487.5 X Primary Examiner—Alan Cohan
Attorney, Agent, or Firm—Ellsworth R. Roston; Charles H. Schwartz

[57] ABSTRACT

Apparatus is provided for regulating the flow of drops of fluid through a conduit. The apparatus includes first means responsive to the flow of fluid through the conduit for producing a turbulence in such flow when the flow is in a steady stream. The first means may include a tube having an inner wall shaped to produce such turbulence in the steady stream or may include a tube and a member disposed in the tube and having an outer wall shaped to produce such turbulence in the steady stream. The first means may be provided with a helical discontinuity to produce a twisting flow of the fluid in the steady stream for creating the turbulence.

Second means are responsive to the flow of fluid in drops for sensing the rate of the drops. The second means may include a light source for directing light to the fluid and a sensor for receiving light from the fluid. Third means adjustably control the rate at which the drops of fluid flow through the conduit. Fourth means are operatively coupled to the second means and the third means for adjusting the third means in accordance with the sensed rate of the fluid drops to maintain the rate of the flow of the drops of fluid through the conduit at a particular value.

When the fluid flows in a steady stream, the second means senses such means and interrupts the fluid flow. Thereafter, the second, third and fourth means again become operative to regulate the rate at which the drops of fluid flow.

16 Claims, 5 Drawing Figures

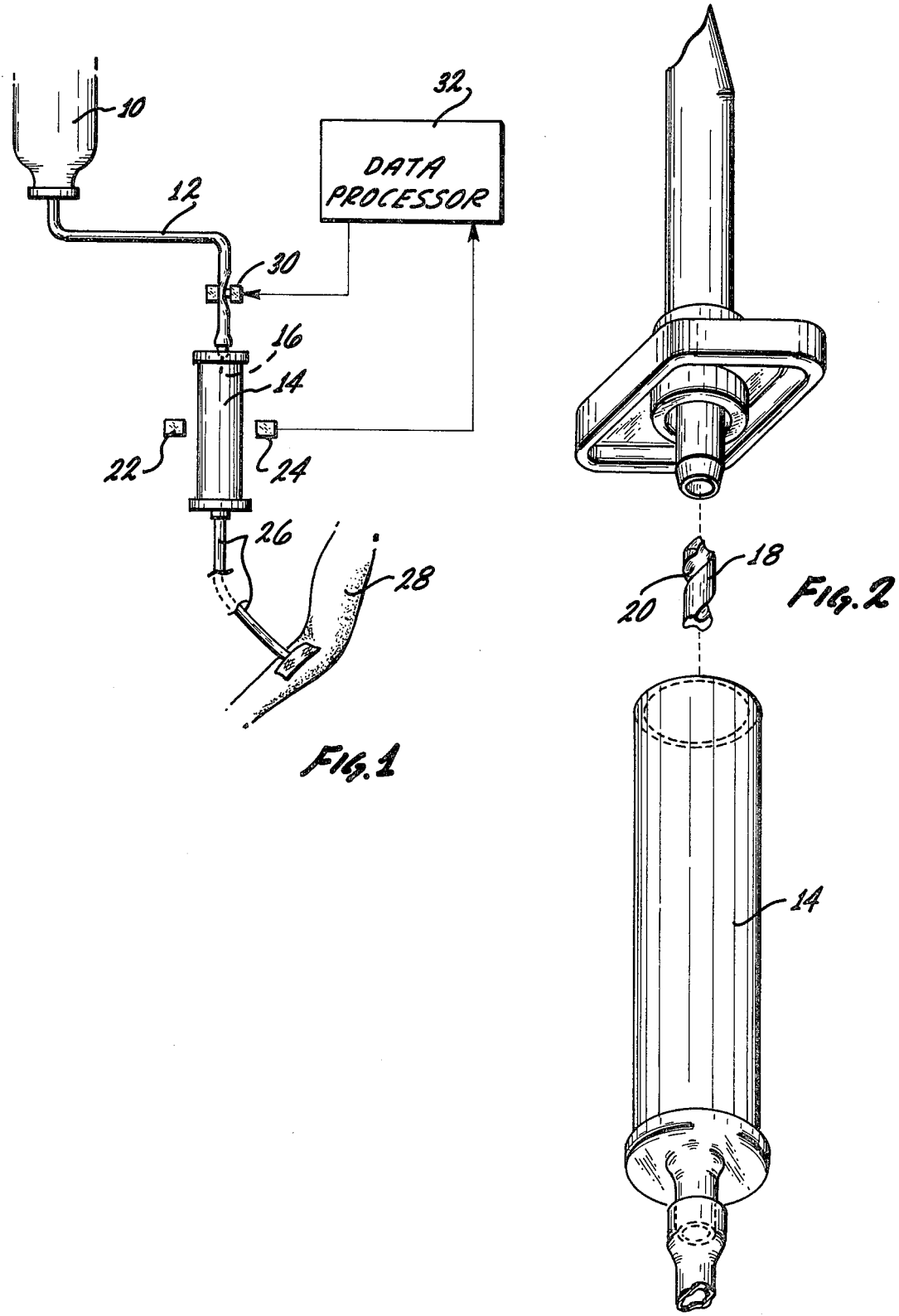

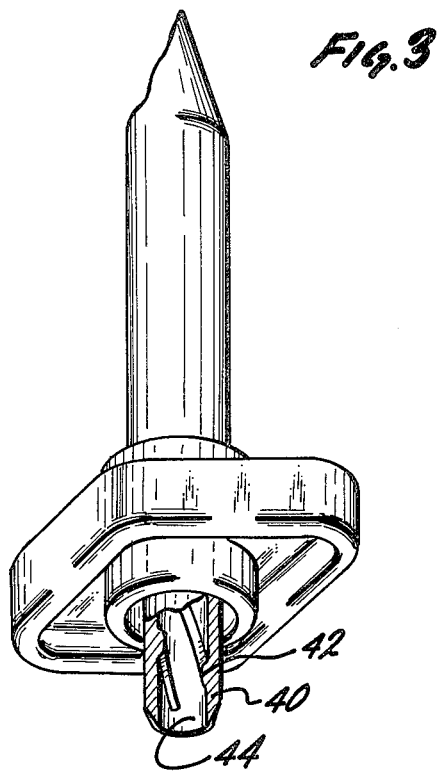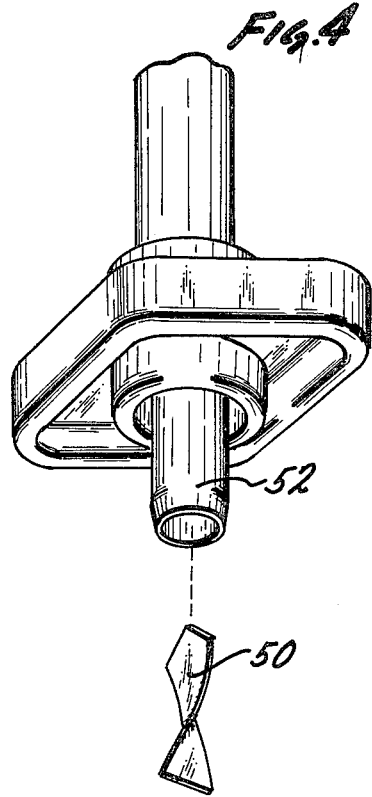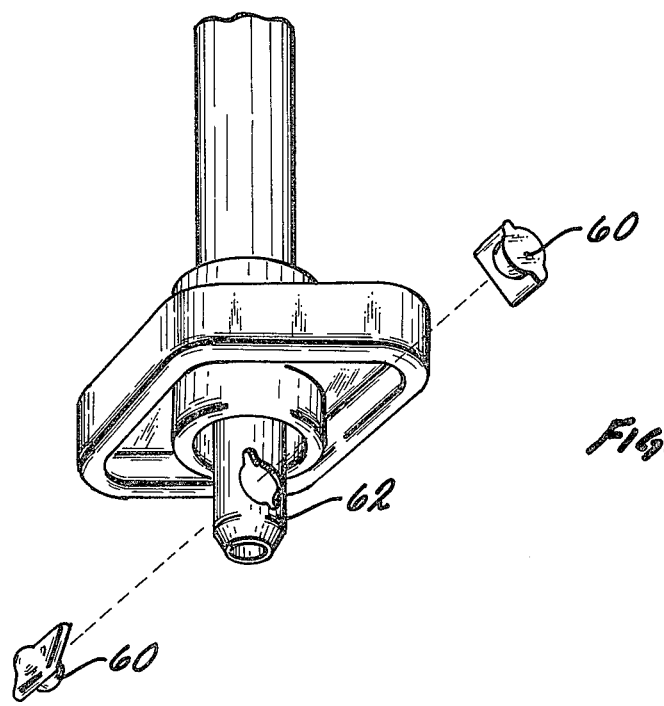

APPARATUS FOR, AND METHOD OF, CONTROLLING THE FLOW OF FLUID

This invention relates to apparatus for regulating the rate at which fluid flows through a conduit. The invention further relates to apparatus for assessing the rate of fluid flow through a conduit in a range including discrete drops and a steady stream, interrupting the flow of fluid in a steady stream and regulating the flow of such fluid when the flow has decreased to a rate providing discrete drops. The invention also relates to methods of regulating such fluid flow.

The flow of drops of intravenous fluid to a patient has to be carefully regulated so that the patient will receive optimum benefit from such intravenous fluid. If the drops of fluid flow to the patient at a rate less than an optimal rate, the patient does not receive sufficient nutritional benefits. If the drops of fluid flow to the patient at an excessive rate, the patient can be injured because the blood vessels of the patient cannot receive an excessive amount of fluid.

Intravenous fluid flows to a patient as drops rather than in a steady stream. If the fluid flows to the patient in a steady stream, the rate tends to be excessive and the patient can become injured. The rate of the flow of drops of intravenous fluid to the patient is dependent upon a number of factors including the age, weight and condition of the patient.

Apparatus is now available for detecting the rate of flow of drops of fluid to a patient and for regulating the rate of such flow within relatively precise limits. The sensing apparatus includes a light source for directing light to the fluid flowing through a conduit and a light sensor for receiving the light from the fluid and for producing a signal in accordance with such reception. Such apparatus further includes equipment for comparing the signals from the sensor with an adjustable reference and for adjusting a clamping member to control the rate at which the drops of fluid flow through the conduit to the patient.

The apparatus now in use has at least one severe limitation. This limitation results because the light source and the light sensor are not able to distinguish between fluid flowing in a steady stream and a complete absence of fluid. As a result, the apparatus now in use considers a steady stream of fluid to be the same as an absence of fluid and accordingly operates to increase the fluid flow. As will be appreciated, the apparatus now in use accordingly presents problems of serious injury to a patient.

In order to be certain that a steady stream of fluid cannot flow to a patient, the range of the regulating apparatus now in use is limited to a relatively narrow range. This prevents the drops of fluid from flowing at a sufficiently high rate to satisfy all of the recuperative procedures which hospitals have adopted.

Various attempts have been made to eliminate the problem of detecting the fluid flowing in a steady stream. In spite of such attempts, the problem still persists. The apparatus presently available is able to detect only discrete drops of fluid so that the range of flow of the fluid drops has to be severely limited.

This application provides apparatus for detecting the flow of fluid whether the fluid flows in drops or in a steady stream. When the fluid flows in drops, the apparatus regulates the flow of the fluid in accordance with such detection so that the drops of fluid flow at a particular rate. For example, when use of the apparatus is made to regulate the flow of intravenous fluid to a patient, the flow of the fluid is regulated at a particular rate of discrete drops. The invention also relates to a method of recognizing the flow of fluid whether the fluid flows in discrete drops or in a steady stream. When the fluid flows in a steady stream, the flow of fluid is interrupted. When the flow of fluid has become interrupted or has decreased to a rate providing discrete drops, the flow of fluid is regulated to provide the flow of the drops of fluid at the desired rate.

The apparatus of this invention includes first means responsive to the flow of fluid through a conduit for producing a turbulence in such flow when the fluid is in a steady stream. The first means may include a tube having an inner wall shaped to produce such turbulence in a steady stream or it may include a tube and a member disposed in the tube and having an outer wall shaped to produce such turbulence in the steady stream. The first means may be provided with a helical discontinuity to produce a twisting flow of the fluid in the steady stream for creating the turbulence.

Second means are responsive to the flow of fluid in drops for sensing the rate of flow of the drops. The second means may include a light source for directing light to the fluid and a sensor for receiving light from the fluid. Third means adjustably control the rate at which drops of fluid flow through the conduit. Fourth means are operatively coupled to the second means and the third means for adjusting the third means in accordance with the sensed rate of the drops of fluid flow to maintain the rate of flow of the drops of fluid through the conduit at a particular value.

When the fluid flows in a steady stream, the turbulence produced by the first means causes the second means to produce a signal for interrupting the steady stream. When the steady stream has been interrupted or has been decreased sufficiently to provide for the flow of discrete drops, the third means and the fourth means become operative to regulate the rate at which the drops of fluid flow.

In the drawings:

FIG. 1 is a schematic elevational view of a system for regulating the flow of drops of fluid through a conduit; and FIGS. 2 through 5 are schematic views, partially in section, of different embodiments of apparatus included in the system of FIG. 1 for producing turbulence in fluid when the fluid flows in a steady stream.

In the embodiment shown in FIGS. 1 and 2, a source 10 of a fluid is provided. When the fluid is to be introduced as intravenous fluid to a patient, the source 10 may be a bottle filled with fluid and disposed above a patient in an inverted relationship. A conduit 12 extends from the source 10. The conduit 12 communicates with a sight tube 14 which may be made from a clear plastic material in a conventional manner.

The conduit 12 is provided with an opening 16 at the end which communicates with the sight tube 14. A cannula 18 is disposed in the opening 16 and is provided with an outer periphery having a discontinuity 20 shaped to produce a turbulence in the fluid flowing from the conduit 12 to the sight tube 14 when the fluid flows in a steady stream. The discontinuity 20 is preferably provided with a helical configuration so as to impart a helical component to the fluid in the steady stream as the fluid flows downwardly through the cannula 18 and into the sight tube 14. This cannula 18 may have a shape corresponding to a drill bit so that the cannula 20 defines a channel for receiving the fluid from the conduit 12 and for directing the fluid downwardly and helically into the sight tube 14.

Sensing means are associated with the sight tube 14 to sense the drops of fluid flowing through the sight tube. The sensing means may include a light source 22 for directing light to the fluid flowing through the sight tube and may also include a light sensor 24 for receiving light from the fluid. The sensor 24 may be disposed on the opposite side of the sight tube from the light source 22 to detect light passing through the tube or it may be disposed on the same side of the sight tube as the light source to receive light reflected or refracted from the fluid in the tube. A conduit 26 communicates with the sight tube 14 to receive the fluid flowing through the sight tube 14. The fluid in the conduit 26 may be directed to a patient 28.

A clamp 30 is coupled to the conduit 12 to control the opening in the conduit 12. The clamp 30 is adjustable in accordance with the operation of a data processor 32 which receives the signals from the sensor 24 and which can be programmed to provide an adjustable reference value for the rate at which the drops of fluid flow through the conduit.

The cannula 18 is provided with characteristics to produce drops of a proper size. For example, a drop having a value to occupy one twentieth of a cubic centimeter has been found to be satisfactory. The provision of the cannula 18 with dimensions for producing drops of satisfactory size can be controlled by varying the depth and width of the discontinuity 20. Drops of the proper size are desirable in providing an optimal volume of fluid to a patient.

When the fluid flows as discrete drops through the conduit 12 and the cannula 18 into the sight tube 14, the cannula 18 does not affect such flow in any way. Furthermore, any helical component imparted to the flow by the discontinuity 20 is relatively small and does not affect the operation of the light source 22 and the sensor 24 in detecting the flow of the drops of fluid through the sight tube 14. This is particularly true when the light source 22 and the sensor 24 are advantageously disposed relative to the sight tube.

The signals produced by the sensor 24 as a result of the flow of such discrete drops of fluid are introduced to the data processor 32. The data processor 32 compares this rate with the rate adjustably preset into the data processor and produces an error signal representing any differences between the actual and desired rates of the flow of the drops of fluid. This error signal is introduced to the clamp 30 to adjust the constraint of the clamp on the conduit 12 so that the actual rate of flow of the drops of fluid becomes equal to the preset rate of such flow.

It may sometimes happen that fluid flows through the conduit 12 in a steady stream. Turbulence is imparted to such flow as the fluid flows through the discontinuity 20 in the cannula 18. Such turbulence is sensed by the sensor 24, which produces a signal representing a high rate of fluid flow. The signals from the sensor 24 are introduced to the data processor 32 and are compared in the data processor 32 with the preset value. The resultant error signals from the data processor 32 are introduced to the clamp 30 to close the clamp on the conduit 18 so that the flow of fluid through the conduit becomes interrupted. When the fluid flow becomes interrupted or at least becomes sufficiently reduced so that discrete drops of fluid again flow through the conduit, the system described above becomes operative again to regulate the flow of these drops at a desired level.

As will be appreciated, the cannula may be produced in a number of different ways. For example, a cannula may be provided as shown in FIG. 3. In this embodiment, a discontinuity is provided on the inner wall of a tube 40 by producing a protuberance 42 in the inner wall of the tube. This protuberance 42 may be helically shaped to define a helical channel 44. When the fluid flows in a steady stream, the channel 44 imparts a swirling motion to the fluid to create a turbulence which is sensed by the sensor as described above.

FIG. 4 illustrates another embodiment for producing turbulence. In this embodiment, a cannula 50 is disposed in a tube 52 to impart turbulence to the flow of fluid through the tube when the fluid flows in a steady stream. The cannula 50 has a different configuration than the cannula 18 in FIG. 2. FIG. 5 illustrates another form of a member 60 which can be introduced into a tube 62 to produce a desired turbulence of fluid when the fluid flows in a steady stream.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for regulating the flow of drops of fluid,
    first means for providing for a flow of the drops of fluid and for producing a turbulence in the flow of fluid from the first means when the flow is in a steady stream,
    second means associated with the first means for receiving the drops of fluid or the turbulently flowing fluid from the first means,
    third means for sensing the drops of fluid and the turbulently flowing fluid in the second means,
    fourth means responsive to a reference level for the flow of the drops of fluid and to the sensed rate of the drops of fluid and the turbulently flowing fluid for providing an output signal, and
    fifth means operatively coupled to the fourth means for adjusting the rate of the flow of the drops of fluid to the reference level in accordance with the characteristics of the output signal for a flow of the fluid in discrete drops and for interrupting the flow of fluid for a flow of the fluid in a steady stream.

2. The combination set forth in claim 1, wherein
    the third means includes a light source for directing light to the second means and a sensor for receiving light from the second means and wherein the fourth means is operatively coupled to the sensor.

3. The combination set forth in claim 1 wherein
    the first means constitutes a tube and a member disposed in the tube and shaped on its outer periphery to provide a turbulence in the flow of fluid in the steady stream through the tube and to direct the turbulently flowing fluid to the second means for sensing by the third means.

4. The combination set forth in claim 1 wherein
    the first means constitutes a tube having a discontinuity in the inner periphery of the tube to produce a turbulence in the flow of fluid in the steady stream through the tube and to direct the turbulently flowing fluid to the second means for sensing by the second means.

5. The combination set forth in claim 1 wherein the first means is shaped to provide a twisting of the fluid as the fluid flows downwardly from the first means to the second means.

6. In combination for regulating the flow of fluid,
first means responsive to the flow of fluid for producing a turbulence in such flow when such flow is in a steady stream,
second means responsive to the flow of the fluid through the first means for determining the rate of the flow of the drops of the fluid,
third means for adjustably controlling the rate at which the drops of fluid flow through the first means, and
fourth means operatively coupled to the second means and the third means for adjusting the third means in accordance with the sensed rate of the fluid flow to maintain the rate of the flow of the drops of fluid at a particular value and for adjusting the third means to interrupt the fluid flow when the fluid flow is in a steady stream.

7. The combination set forth in claim 6 wherein the second means includes a light source for directing light to the flowing fluid and includes a light sensor for producing a signal in accordance with the rate of fluid flow and wherein
the fourth means is responsive to the signal from the sensor to adjust the third means to maintain the flow of the fluid at the particular value for discrete drops of fluid flow and to interrupt the fluid flow for the flow of fluid in a steady stream.

8. The combination set forth in claim 6 wherein the first means includes a member having an outer surface shaped to produce a turbulence in the flow of fluid through the first means when the fluid flows in a steady stream and the first means further includes a tube holding the member within the tube.

9. The combination set forth in claim 8 wherein the outer surface of the member is provided with a helical discontinuity to produce a helical component to the flow of the fluid and wherein
the second means includes a light source for directing light to the flowing fluid and includes a light sensor for producing a signal in accordance with the rate of fluid flow.

10. The combination set forth in claim 6 wherein the first means includes a tube having an inner surface shaped to produce a turbulence in the flow of fluid through the tube when the fluid is flowing in a steady stream.

11. The combination set forth in claim 10 wherein the inner surface of the tube is provided with a helical discontinuity to produce a helical component to the flow of the fluid.

12. A method of regulating the flow of fluid through a conduit, including the following steps:
providing for a flow of fluid in drops or in a steady stream,
detecting the flow of fluid in drops and in the steady stream,
adjusting the rate of flow of the fluid in the drops to a particular rate in accordance with the detected rate of flow of the fluid in the drops and interrupting the flow of fluid in the steady stream, and
wherein turbulence is produced in the flow of fluid in the steady stream and the turbulence in the flow of fluid in the steady stream is detected to obtain an interruption in the flow of fluid.

13. A method as set forth in claim 12 wherein the turbulence is produced by imparting a helical compenent to the flow of fluid in the steady stream.

14. A method of regulating the flow of fluid through a conduit, including the following steps:
providing for a flow of fluid in a range including drops and a steady stream,
converting the flow of fluid in the steady stream into a turbulent flow,
determining the rate at which the drops of the fluid flow through the conduit,
varying the rate of the flow of the drops of fluid to maintain the rate of flow of the drops of fluid at a particular value, and
interrupting the flow of fluid in the turbulent state.

15. A method as set forth in claim 14 wherein a helical component is imparted to the direction of fluid flow to create the turbulent flow of the fluid in the steady stream.

16. A method as set forth in claim 15 wherein the rate of flow of the drops of fluid and the turbulence are determined by directing light toward the fluid and by sensing the light from the fluid.

* * * * *